United States Patent [19]

Fischer

[11] Patent Number: 5,599,835
[45] Date of Patent: Feb. 4, 1997

[54] USE OF DL-LIPOIC ACID AS A MEDICAL FOOD IN THE TREATMENT OF DIABETES MELLITUS

[76] Inventor: Frederick B. Fischer, 6685 Phillips Mill Rd., Box 6, Solebury, Pa. 18963

[21] Appl. No.: 344,131

[22] Filed: Nov. 23, 1994

[51] Int. Cl.$^6$ ....................................... A01N 43/26
[52] U.S. Cl. ............................................. 514/440
[58] Field of Search ............................................. 514/440

[56] References Cited

PUBLICATIONS

CA 104:161793 1985.
CA 101:495 1984.
Medline 95094966 (1994).
Medline 93093519 (1992).
CA 86:177214 (1977).

Primary Examiner—Paul J. Killos
Attorney, Agent, or Firm—Mathews, Woodbridge & Collins

[57] ABSTRACT

The object of the invention is the use and inclusion of DL-lipoic acid in a physician supervised, orally administered, modular-formula medical food in the management and treatment of a metabolic disorder, more specifically, a metabolic aberration of the multi-enzyme complex of pyruvate dehydrogenase, symptomatic of diabetes mellitus.

1 Claim, No Drawings

USE OF DL-LIPOIC ACID AS A MEDICAL FOOD IN THE TREATMENT OF DIABETES MELLITUS

FIELD OF THE INVENTION

Diabetes mellitus is a chronic syndrome of impaired carbohydrate, protein and fat metabolism secondary to insufficient secretion of insulin. It occurs in two major forms: insulin-dependent diabetes mellitus (type I) and non-insulin-dependent diabetes mellitus (type II). Essential to pivotal enzymatic reactions in intermediary metabolism are known nutrients, fatty acids and minerals that are utilized as coenzymes and cofactors. An initial step of the Embden-Meyerhof pathway in the oxidation of glucose is phosphorylation, which is the addition of phosphorus to glucose, trapping glucose and forming the compound glucose-6-phosphate, which initiates a sequence of reactions leading to the formation of pyruvate, the terminative product of the glycolytic pathway. Pyruvate dehydrogenase is a multi-enzyme complex positioned at the terminal juncture of glycolysis. The overall reactions of pyruvate dehydrogenase allow for a forming of acetyl coenzyme A from pyruvate, the final energy product of the glycolytic pathway. Acetyl coenzyme A is the initial step of the Krebs cycle (also called the citric acid cycle or tricarboxylic acid cycle) that is the final common pathway of all nutrient metabolites involved in energy production.

The oxidative processing of glucose to pyruvate requires completion of the reactions of the pyruvate dehydrogenase complex, and the enzyme reactions are dependent upon intracellular and molecular availability of nutrients, primarily the nutrients lipoic acid, thiamine, riboflavin, niacin, pantothenic acid and magnesium. The unavailability of any single nutrient product would impair the mechanism of anaerobic enzymatic conversion of glucose to pyruvate. Therefore, the use and inclusion of nutrients possessing activities interrelated to lipoic acid in the sequence of enzymatic reactions of the pyruvate dehydrogenase complex significantly enhances the sustenance value of a modular-formula medical food.

Lipoic acid is an essential nutrient and coenzyme which functions with close similarity to thiamine in the initial decarboxylation step of pyruvate. Lipoic acid has two sulfur bonds that combine with thiamine to form thiamine pyrophosphate [TPP] to participate in a key reaction of oxidative decarboxylation to reduce pyruvate to active acetate, thereby allowing for forming of acetyl coenzyme A and its entry into the Krebs cycle, the final energy cycle.

The sequence of reactions resulting in the forming of acetyl coenzyme A is the most complex in carbohydrate metabolism, and the most pivotal in cell energy metabolism. The forming of acetyl coenzyme A is dependent on no less than six nutrients: four B vitamins, one related fatty acid factor, and a mineral element in the form of ionized magnesium (Mg++). The cofactors participating in enzymatic reactions include thiamine pyrophosphate, which is a product of thiamine; coenzyme A, which is derived from pantothenic acid; nicotinamide-adenine dinucleotide (AND), which is yielded by niacin; and lipoic acid.

Modular-Formula Medical Food—The invention relates to a medical food that is a specially formulated composition of essential nutrients and other special dietary requirements to be consumed or administered under medical supervision in the treatment or management of patients displaying a metabolic disorder symptomatic of diabetes mellitus. The well-established definition of a medical food is that of a formulated food for use as either the exclusive or a supplemental source of nutrition for patients with limited or impaired capacity to ingest, digest, absorb, or metabolize ordinary foodstuffs or certain nutrients contained therein, or have other specific nutrient requirements where dietary management cannot be achieved by modification of the normal diet or by other foods for special dietary uses. Medical foods originated under the Orphan Drug Act (U.S. Congress, 1988), and were further defined under the Nutrition Labeling and Education Act (U.S. Congress, 1990); Paragraph (5) (A) (iv) "The term 'medical food' means a food that is formulated to be consumed or administered enterally under the supervision of a physician and that is intended for the specific dietary management of a disease or condition for which distinctive nutritional requirements, based on recognized scientific principles, are established by medical evaluation."

The definition makes clear that medical foods are foods that are specifically and specially formulated and processed (as opposed to naturally occurring foodstuffs used in their natural state). They are for the partial or exclusive feeding of a patient who is seriously ill or who requires the product as a major treatment modality. Medical foods are fed by means of oral intake or by enteric feeding via tube infusion; that is, medical foods provide nutrition via the gastrointestinal tract, by mouth, or through a tube or catheter that delivers nutrients beyond the oral cavity.

Medical foods are distinguished from foods for special dietary uses or from foods that make health claims by the requirement that medical foods must be used under medical supervision. The intended use of a medical food is for the dietary management of a patient receiving active and ongoing medical supervision, and the medical food is determined by the physician as a requirement to overall medical care.

The medical-food category is further defined through five sub-classifications: nutritional-complete formulas, intended to provide all nutrients necessary for sustaining life viability; modular formulas, intended as prepared diets for mitigation or management of a disease; special products for inborn errors of metabolism, for correction of metabolic deficiencies from birth; oral rehydration solutions, to correct dehydration; and very low-calorie diets (less than 400 kcal/d), a regimen for special diets. This definition of medical foods classifies the invention as a modular formula of orally administered DL-lipoic acid and related nutrients intended to mitigate a medical condition which is a metabolic disorder of the multi-enzyme complex of pyruvate dehydrogenase.

SUMMARY OF THE INVENTION

The present invention is a novel method for the management of a metabolic disorder expressed as diabetes mellitus, which is a syndrome of impaired carbohydrate, protein and fat metabolism secondary to insufficient secretion of insulin.

The method of the invention is the use of DL-lipoic acid in co-administration with other nutrients that are also essential to the multi-enzyme reactions of the pyruvate dehydrogenase complex. Furthermore, the invention is that of a composition as a modular-formula medical food for oral administration under the direction and supervision of a physician in the treatment, management or correction of a metabolic disorder that is indicative of diabetes mellitus.

It is well documented that lipoic acid, and lipoic acid in reduced form as dihydrolipoic acid, is required in the oxidative decarboxylation of alpha-keto acids, such as pyruvate, that are important intermediates in the citric acid cycle and in amino acid metabolism. The enzyme system that catalyzes the overall reaction, namely, the pyruvate dehydrogenase complex, contains protein-bound thiamine pyrophosphate, flavin adenine nucleotide (AND) and lipoic acid as essential coenzymes.

Nutrients central to intermediary metabolism and, more specifically, central to key enzyme reactions of the pyruvate dehydrogenase complex, are thiamine, utilized in the form of thiamine pyrophosphate; riboflavin, participating as flavin adenine dinucleotide (FAD); niacin, serving as a source of nicotinamide-adenine dinucleotide (AND); pantothenic acid, utilized in the form of acetyl coenzyme A; lipoic acid; biotin; inositol; choline; and the mineral magnesium. The availability of ionized magnesium is a requirement in the forming of thiamine pyrophosphate. In the presence of magnesium ions, the reactions of pyruvate decarboxylase and alpha-ketoglutarate decarboxylase are completed to form the active enzyme thiamine pyrophosphate.

Lipoic acid is a nutrient and coenzyme that is essential to intermediary metabolism, and is historically identified as a fat-soluble B-vitamin. By chemical description, lipoic acid is a fat-soluble, sulfur-containing fatty acid. Lipoic acid is synthesized in trace quantities by the body, and food sources of the nutrient are liver, soybeans, pancreas, green leafy vegetables and yeast.

Within the scope of the invention is use of either the naturally occurring R and S lipoic acid or of the synthetic DL-lipoic acid as an ingredient of a prepared formulation for the treatment of a metabolic disorder associated with diabetes. The invention pertains to the use of DL-lipoic acid in a composition of essential nutrients which participate in the enzymatic reactions comprising the pyruvate dehydrogenase complex, and to the administration of this composition, under the supervision of a physician, as a modular-formula medical food to patients for a specific disease.

The ingredients of the modular-formula medical food are to be in the physical form of tablets or capsules for the benefit of oral administration. The manufacturing process is the combining of dry, free-flowing ingredients with compressible excipients and other additives that are well-established in the dietary supplement and pharmaceutical arts in order to attain a palatable preparation in the form of a tablet or capsule with the appropriate physical properties and characteristics for such dosage forms. The modular-formula medical food could also be in the form of a free-flowing powder consisting of excipients, flavors, flowing agents and other matter described in prior art for powdered formulations intended for ingestion. The composition of a modular-formula medical food could consist of, in addition to DL-lipoic acid, nutrients with known activity within the multi-enzyme complex of pyruvate dehydrogenase. Such nutrients are thiamine, riboflavin, niacin, biotin, pantothenic acid, as well as fatty acids, and the mineral magnesium. The invention does not preclude other nutrients or matter with biological activity in the reactions of the pyruvate dehydrogenase complex from being used in a composition of a modular-formula medical food.

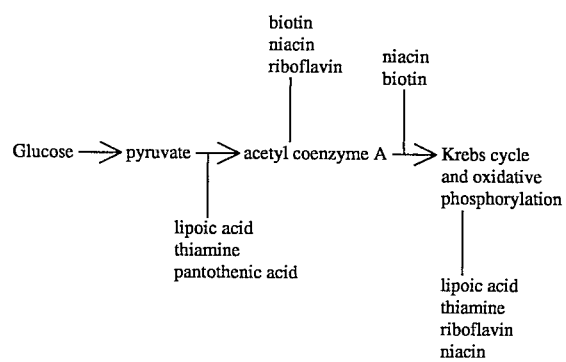

DETAILED DESCRIPTION OF THE INVENTION

The Embden-Meyerhof pathway (of glucose metabolism) comprises a sequence of enzymatic reactions for oxidative conversion of glucose to the final metabolite, pyruvate. Pivotally positioned at the terminus of glycolysis is the multi-enzyme complex of pyruvate dehydrogenase, which catalyzes the overall reaction of pyruvate and forming of acetyl coenzyme A, which enters the Krebs cycle. The total nutrient requirements of the reactions of the pyruvate dehydrogenase complex are nicotinamide adenine dinucleotide, thiamine pyrophosphate, lipoic acid, coenzyme A, and ionized magnesium. Elsewhere, lipoic acid participates within the tricarboxylic acid cycle in the releasing of energy from products of protein and fat metabolism.

DL-lipoic acid is the oxidized disulfide form of 6,8-dithioctanic acid. The chemical designation is 1,2-dithiolane 3-valeric acid. The role of lipoic acid in metabolic viability via oxidation of alpha-keto acid dehydrogenase complexes, specifically the biochemical reactions of the pyruvate dehydrogenase complex, is significant.

Lipoic acid is widely distributed among plants and animals in a protein-bound form. In literature, lipoic acid is identified as an essential nutrient and as an essential coenzyme for occurrence of coenzymatic reactions of intermediary metabolism. The coenzyme function of lipoic acid is in the oxidative decarboxylation of alpha-keto acids. Alpha-keto acid dehydrogenases have been found to represent multi-enzyme complexes. The chemical aspect of the coenzymatic action of lipoic acid is in the decarboxylation and oxidation of alpha-keto acids within the complexes.

Lipoic acid is transiently reduced to dihydrolipoic acid and this reduced form is also a substrate for the pyruvate dehydrogenase complex in the oxidative decarboxylation of alpha-keto acids, principally pyruvate. The pyruvate dehydrogenase complex is a multi-enzyme complex that catalyzes the following overall reactions: pyruvate+AND+ CoA−SH=acetyl CoA+$CO_2$+NADH. The complex consists of three enzymes: pyruvate dehydrogenase (lipoamide), dihydrolipoamide acetyltransferase, and dihydrolipoamide dehydrogenase. Furthermore, five types of cofactors have been isolated from the multi-enzyme complex: (1) a thiamine pyrophosphate-containing decarboxylase, (2) a lipoic acid-containing lipoic acid reductase transacylase, (3) a flavin adenine dinucleotide (FAD)-containing lipoamide oxidoreductase, (4) an oxidized form of nicotinamide adenine dinucleotide and (5) acetyl coenzyme A, a thiol ester of coenzyme A and acetic acid (From ultracentrifugal analysis and quantitative determination of coenzyme content, it has been concluded that pyruvate dehydrogenase consists of 12 molecules of pyruvate decarboxylase, 6 molecules of lipoamide oxidoreductase and 1 aggregate of lipoic acid reductase transacetylase. Lipoamide oxidoreductase contains 2 moles of FAD per mole of enzyme and lipoic acid reductase transacetylase contains 1 mole of protein-bound lipoic acid per 35,000 g of protein.).

The biochemical aspect of lipoic acid is to mediate the transfer of electrons and activated acyl groups resulting from the decarboxylation and oxidation of alpha-keto acids within the complexes. In this process, lipoic acid is itself transiently reduced to dihydrolipoic acid, and in this reduced form is the acceptor of the activated acyl groups. This dual role of electron and acyl-group acceptor enables lipoic acid to couple the two processes.

Lipoic acid is the coupler of electron and group transfers catalyzed by the alpha-ketoglutarate dehydrogenase complex. The pyruvate dehydrogenase and alpha-ketoglutarate dehydrogenase complexes are centrally involved in the metabolism of carbohydrates by the glycolytic pathway and the tricarboxylic acid cycle (Krebs cycle). They catalyze two of the three decarboxylation steps in the complete oxidation of glucose, and they produce NADH (reduced form of nicotinamide adenine dinucleotide) and activated acyl compounds from the oxidation of the resulting aldehydes.

Lipoic acid, like thiamine and biotin, contains sulfur. Lipoic acid with two sulfur bonds combines with the thiamine-containing enzyme pyrophosphatase to reduce pyruvate to active acetate. Lipoic acid is covalently linked to the enzymes that require it through a peptide bond with the amino group of lysine. In the reduced form of dihydrolipoic acid it participates as a coenzyme in the oxidative decarboxylation of alpha-keto acids to aldehydes. This is also true of thiamine in the form of pyrophosphate. Key biochemical reactions involve pyruvate, which is metabolized to acetyl coenzyme A, and alpha-ketoglutarate, which is metabolized to succinyl coenzyme A, a high-energy intermediate formed in the tricarboxylic acid cycle by the oxidation of alpha-ketoglutaric acid. Lipoic acid is a fat-soluble vitamin, this in accordance with its chemical properties. The water-soluble vitamins have proven to be catalysts involved in various phases of intermediary metabolism, e.g. electron transport, transamination and formation of carbon-carbon bonds. The role of lipoic acid is well-defined as that of a participant in essential metabolic reactions, namely oxidation and reduction. An element of the function of lipoic acid is performing electron transport and acetyl transfer, a link between a redox system and a high-energy bond. Lipoic acid also falls within the definition of a coenzyme, which is typically covalently bound to its enzyme system. In this way it becomes, under physiological conditions, water-soluble, and by this very nature is part of intermediary metabolism. Pyruvate formed in the glycolytic pathway is primarily decarboxylated to a 2-carbon fragment (active acetate).

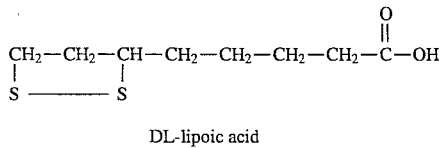

DL-lipoic acid

Description: An asymmetric carbon atom is present, and only the (+) form is metabolically active. Lipoic acid is the oxidized disulfide form of 6,8-dithioloctanoic acid. The chemical designation is 1,2-dithiolane-3-valeric acid.

Enzyme reactions involving lipoic acid and lipoic acid in reduced form (dihydrolipoamide) are summarized here. Pyruvate dehydrogenase is a multi-enzyme complex that catalyzes the reaction: pyruvate+AND+CoA–SH=acetyl CoA+$CO_2$+NADH. The complex consists of three enzymes: pyruvate dehydrogenase, dihydrolipoamide acetyltransferase and dihydrolipoamide. The complex requires five cofactors: thiamine pyrophosphate, lipoic acid, coenzyme A, flavin adenine dinucleotide and nicotinamide adenine dinucleotide. The reactions occur in the mitochondria and produce acetyl coenzyme A by fatty-acid synthesis for subsequent oxidation to $CO_2$ and water in the tricarboxylic acid cycle. A deficiency of any component of the enzyme complex incurs a metabolic imbalance.

Mechanism of Pyruvate Oxidation

Oxidation is carried out through the electron-transport chain, the electron acceptor being NAD. The overall reaction is represented as follows:

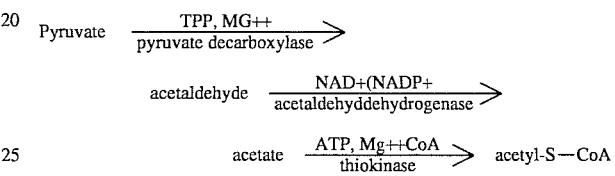

This reaction has a relatively low free-energy change. The formation of acetyl coenzyme A is important, since this allows the acetate unit (pyruvate) to be fed directly into the Krebs cycle. Lipoic acid is required for NAD in oxidative decarboxylation of pyruvate.

The scope of the invention is the use, within the composition of a modular-formula medical food, of DL-lipoic acid and other nutrients and matter that are interrelated by activity to lipoic acid in vital metabolic processes, and where co-administration of DL-lipoic acid and such other essential nutrients and matter are therapeutically useful.

The ingredients of a modular-formula medical food, in addition to DL-lipoic acid, include, but are not limited to: (1) Thiamine, 3-[(4-amino-2-methyl-5-pyrimidinyl)methyl]-5-(2-hydroxyethy)-4-methylthiazolium. In the active form of thiamine pyrophosphate it participates in the oxidative decarboxylation of alpha-keto acids to aldehydes. The most important substrate for this type of reaction is pyruvate, which is metabolized to acetyl coenzyme A and alpha-ketoglutarate, which is metabolized to succinyl coenzyme A. Both of these reactions require the participation of thiamine pyrophosphate, lipoic acid and niacin adenine dinucleotide (NAD). Synthetically formed thiamine hydrochloride or thiamine mononitrate may be ingredients of a modular-formula medical food. (2) Riboflavin, 6,7-dimethyl-9-[1'-D-ribityl]-isoalloxazine. Serves as a component of two coenzymes, the flavoproteins flavin adenine dinucleotide (FAD), which functions as a hydrogen carrier in oxidation-reduction processes, and riboflavin 5'-phosphate (FMN). Riboflavin 5'-phosphate (FMN) and adenosine 5'-phosphate are linked by a pyrophosphate bond. FMN acts as a coenzyme in the multi-enzyme complexes of the pyruvate dehydrogenase. (3) Niacin, nicotinic acid. A constituent of the redox coenzymes nicotinamide adenine dinucleotide (NAD) and nicotinamide adenine dinucleotide phosphate (NADP), which are involved in the multi-enzyme reactions of the pyruvate dehydrogenase complex. (4) Pantothenic acid, the amide of beta-alanine and pantoic acid, is a constituent of two enzymes: coenzyme A and phosphopantetheine. (5) Biotin, 2'-keto-3,4-imidazolido-2-tetrahydrothiophenedelta-n-valeric acid. Participates in carboxylation, with an amino group of lysine, in enzymatic reactions involving the four enzymes: acetyl-CoA carboxylase, pyruvate carboxylase, propionyl-CoA carboxylase, and beta-methylcrotonyl-CoA carboxylase. (6) Magnesium: Salts of magnesium are essential to the multi-enzyme complexes of oxidative phosphorylation.

What is claimed:

1. A method of treating a patient suffering from a chronic syndrome of impaired carbohydrate, protein and fat metabolism characteristic of diabetes mellitus comprising administering to a patient a therapeutically effective amount of a medical food comprising lipoic acid and thiamine.

* * * * *